United States Patent [19]
Arakawa et al.

[11] 4,037,463
[45] July 26, 1977

[54] TEMPERATURE-DETECTING ELEMENT

[75] Inventors: Yoshiaki Arakawa; Isamu Aoyanagi; Saburo Matsumoto, all of Yokohama, Japan

[73] Assignee: Showa Denko Kabushiki Kaisha, Tokyo, Japan

[21] Appl. No.: 594,070

[22] Filed: July 8, 1975

[30] Foreign Application Priority Data
July 10, 1974 Japan .................................. 49-78968
July 30, 1974 Japan .................................. 49-87142

[51] Int. Cl.² .......................... G01K 3/06; G01K 7/04; G08B 17/00
[52] U.S. Cl. .................... 73/341; 73/359 R; 340/227 C
[58] Field of Search .................... 73/340-342, 73/359-361; 136/228, 230; 338/26, 28; 340/227 C

[56] References Cited
U.S. PATENT DOCUMENTS

| | | | |
|---|---|---|---|
| 2,805,272 | 9/1957 | Postal | 136/228 |
| 2,944,422 | 7/1960 | Wald | 73/342 |
| 2,996,916 | 8/1961 | Smith | 73/341 |
| 3,018,663 | 1/1962 | Dunlop | 73/341 |
| 3,307,401 | 3/1967 | Bachman | 73/359 |
| 3,408,607 | 10/1968 | Davis | 338/26 |
| 3,444,740 | 5/1969 | Davis | 73/341 X |
| 3,472,073 | 10/1969 | Irani | 73/360 |
| 3,493,949 | 2/1970 | Servos et al. | 340/227 C X |
| 3,514,998 | 6/1970 | Benson | 73/359 X |
| 3,643,245 | 2/1972 | Jones et al. | 340/227 C X |
| 3,665,766 | 5/1972 | Johnston | 73/342 |
| 3,744,555 | 7/1973 | Fletcher et al. | 73/342 X |
| 3,750,471 | 8/1973 | Bremer | 73/342 |
| 3,966,500 | 6/1976 | Brixy | 73/362 AR X |

Primary Examiner—Richard C. Queisser
Assistant Examiner—John S. Appleman
Attorney, Agent, or Firm—Kemon & Estabrook

[57] ABSTRACT

A temperature-detecting element which comprises two metal wires jointly forming a thermocouple and a plurality of electric resistors disposed between said two metal wires, thereby detecting a mean temperature in a given region or abnormal local temperature changes therein.

20 Claims, 27 Drawing Figures (A)

(B)

(C)

(D)

(A)   (B)

TEMPERATURE-DETECTING ELEMENT

BACKGROUND OF THE INVENTION

This invention relates to a temperature-detecting element for detecting a mean temperature in a given region or abnormal local temperature changes therein.

Where the mean temperature of a given region is measured, for example, where the mean atmospheric temperature is determined to define the coefficient of through heat transfer of structural material in order to evaluate the physical properties of said structural material, then customary practice is to measure temperatures at a plurality of sites within said region and average the measured values to provide a mean temperature. Abnormal local temperature rise or fall in a region resulting from, for example, occurrence of a fire, leakage of molten metal from an electric furnace, damage or corrosion of the interior material of a reactor or gas leakage from an LNG tank is determined likewise by measuring temperatures at a plurality of sites within the region and comparing the measured values.

To date, measurement of temperatures at a plurality of (for example, an $n$ number of) sites has been effected by setting an $n$ number of, for example, thermocouples, thermistors, electro-resistance thermometers or mercury thermometers at said sites.

If a thermocouple, a thermistor, or an electric-resistance thermometer is to be used as a temperature-detecting element, a total of $2n$ number of lead wires have to be provided for the temperature-detecting elements set at $n$ number of sites As the sites of measurement increase in number, the lead wires intricately intersect each other, presenting difficulties in their connection or probably giving rise to errors in said connection. Further, it is necessary to install an $n$ number of meters to find measured values of temperature or a multicircuit changeover switch, presenting considerable inconvenience in practical application. Particularly application of a thermally sensitive resistor as a temperature detecting element is accompanied with the disadvantage of providing an external constant voltage power source. Where a mercury thermometer is used, a temperature-measuring worker must have an access to each site of measurement to find a measured value of temperature thereof. Particularly, where the worker has to measure the temperature of the open air, his access to a given site appreciably affects the temperature of said site, failing to carry out an accurate measurement.

A recent improved thermocouple consists of a multi-junction type in which one of the metal wires constituting a thermocouple is used as a common conductor. Even this improvement only has the effect of decreasing the number of metal wires from $2n$ to $(n + 1)$, little contributing to the resolution of other problems referred to above.

Further where measurement is made of the temperature of the surface of an object, a scanning type infrared thermometer or infrared camera is used. However, such temperature determining device is expensive, demands a considerable skill of an operator, and is moreover accompanied with the disadvantage of requiring an operator to judge the result of detection by the naked eye on the screen.

SUMMARY OF THE INVENTION

It is accordingly an object of this invention to provide a highly sensitive temperature detecting element of simple arrangement.

Another object of the invention is to provide a temperature-detecting element capable of directly measuring the mean temperature of any desired region.

Still another object of the invention is to provide a temperature-detecting element capable of directly detecting abnormal local temperature changes in said region.

Further objects and scopes of the invention will be understood by reference to the following description.

The above-mentioned objects have been attained by a temperature-detecting element which comprises two metal wires jointly forming a thermocouple and electric resistor units disposed between said two metal wires, the definition of said electric resistor units being given later.

DETAILED DESCRIPTION OF THE INVENTION

Figure 1:
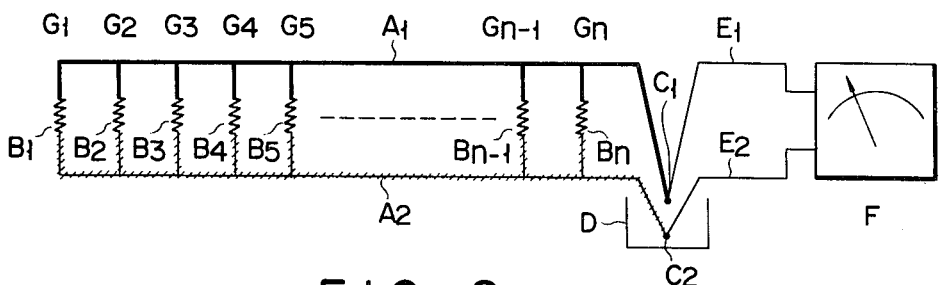
FIG. 1 is a schematic circuit arrangement containing a temperature-detecting element according to this invention, illustration the principle of the invention.

The principle of this invention will now be described by reference to FIGS. 1 to 3. Now let us take the example of an element which is formed, as shown in FIG. 1, of a pair of metal wires $A_1$, $A_2$, such as a chromel wire and alumel wire jointly constituting a thermocouple and an n number of electric resistors $B_1$ to $B_n$ connected in parallel between said metal wires $A_1$, $A_2$. One end $C_1$ of one of the paired metal wires $A_1$, $A_2$ and one end $C_2$ of the other of said wires $A_1$, $A_2$ are kept at the known level of temperature, for example, 0° C by a cold junction compensator D. Said ends $C_1$, $C_2$ are connected to an electric meter F through the corresponding lead wires $E_1$, $E_2$.

According to the above-mentioned circuit arrangement, those parts of the paired metal wires $A_1$, $A_2$ between which the electric resistors are disposed and the ends $C_1$, $C_2$ of said metal wires $A_1$, $A_2$ which are kept at known level of temperature constitute an n number of thermocouples $G_1$ to $G_n$. The thermocouples $G_1$ to $G_n$ give forth electromotive forces corresponding to temperatures $T_1$ to $T_n$ in the regions in which the electric resistors $B_1$ to $B_n$ are disposed. Said thermoelectric motive forces are supplied to the meter F.

Figure 2:
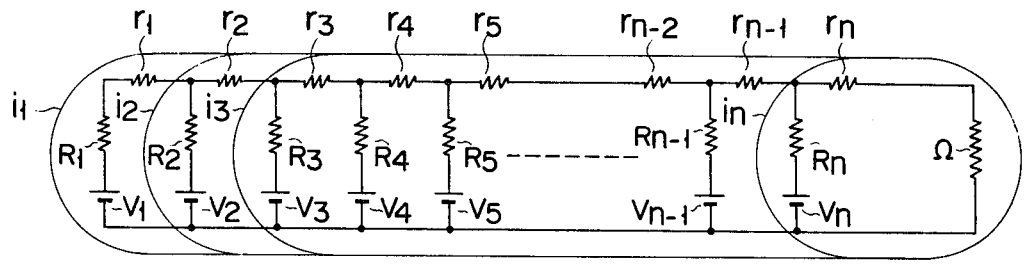
FIG. 2 is an equivalent circuit to that of FIG. 1.

Therefore, with $V_1$ to $V_n$ taken to denote the thermoelectric motive forces generated by the thermocouples $G_1$ to $G_n$ according to the temperatures $T_1$ to $T_n$, $r_1$ to $r_{n-1}$ taken to show the sums of the electric resistances of the paired metal wires $A_1$, $A_2$ occurring between the adjacent electric resistors $B_1$ to $B_n$, $r_n$ taken to represent a sum of resistances occurring in the paired metal wires $A_1$, $A_2$ between the electric resistor $B_n$ and the aforesaid one end $C_1$ of the metal wire $A_1$ and also between the electric resistor $B_n$ and the aforesaid one end $C_2$ of the metal wire $A_2$, $R_1$ to $R_n$ taken to indicate the resistances of the electric resistors $B_1$ to $B_n$, and $\Omega$ taken to show internal impedance of the electromotive force meter F, then an equivalent circuit will be obtained, as shown in FIG. 2, in which an n number of series circuits consisting of an n number of D.C. power sources $V_1$ to $V_n$ and resistors $R_1$ to $R_n$ and resistor $\Omega$ are connected in parallel with the resistors $r_1$ to $r_{n-1}$ disposed between every adjacent parallel connected series circuits with the resistor $r_n$ positioned between the last series circuit and resistor $\Omega$.

If loop currents $i_1$ to $i_n$ are chosen to take the courses shown in FIG. 2, then the following equations will result:

$$V_1 = (R_1 + \sum_1^n r_n + \Omega)i_1 + (\sum_2^n r_n + \Omega)i_2 + \dots$$
$$+ (\sum_{n-1}^n r_n + \Omega)i_{n-1} + (r_n + \Omega)i_n$$
$$V_2 = (\sum_2^n r_n + \Omega)i_1 + (R_2 + \sum_2^n r_n + \Omega)i_2 + \dots$$ (1)

$$+ (\sum_{n-1}^n r_n + \Omega)i_{n-1} + (r_n + \Omega)i_n$$
$$\dots$$
$$V_n = (r_n + \Omega)i_1 + (r_n + \Omega)i_2 + \dots$$
$$+ (r_n + \Omega)_{n-1} + (R_n + r_n + \Omega)i_n$$

Then the voltage of an electromotive force indicated on the meter F may be expressed by the following equation:

$$V = \Omega \times \sum_1^n i_n \quad (2)$$

Relationship between the voltage V indicated on the meter F and the thermoelectric motive forces $V_1$ to $V_2$ generated by the thermocouples $G_1$ to $G_n$ may be determined from the above equations (1) and (2) as follows.

Now, the following condition is set:

$$\Omega >> \sum_1^n r_n > \sum_2^n r_n > \dots \sum_{n-1}^n r_n > r_n \quad (3)$$

to determine in a simple form the relationship between the voltage V indicated on the meter F and the thermal electromotive forces $V_1$ to $V_n$ generated by the thermocouples $G_1$ to $G_n$. If the previous equation (1) are rewritten under the above condition, then the following approximation equations will result $$V_1 = (R_1 + \sum_1^n r_n + \Omega)i_1 + \Omega i_2 + \dots + \Omega i_{n-1} + \Omega i_n$$
$$= (R_1 + \sum_1^n r_n)i_1 + \Omega \times \sum_1^n i_n$$
$$V_2 = (R_2 + \sum_2^n r_n)i_2 + \Omega \times \sum_1^n i_n \quad (4)$$
$$\dots$$
$$V_n = (R_n + r_n)i_n + \Omega \times \sum_4^n i_n$$

Then the relationship between the aforesaid voltage V and thermal electromotive forces $V_1$ to $V_n$ may be determined from the above equations (4) and (2) as follows:

$$(V_1 - V)/(R_1 + \sum_1^n r_n) = i_1$$
$$(V_2 - V)/(R_2 + \sum_2^n r_n) = i_2 \quad (5)$$
$$\dots$$
$$(V_n - V)/(R_n + r_n) = i_n$$

From these equations (5) and the previous equations (2) will result the following equations $$\frac{V_1 - V}{R_1 + \sum_1^n r_n} + \frac{V_2 - V}{R_2 + \sum_2^n r_n} + \dots + \frac{V_n - V}{R_n + V_n} = \sum_2^n i_n = \frac{V}{\Omega} \quad (6)$$

$$\therefore \frac{\dfrac{V_1}{R_1 + \sum_1^n r_n} + \dfrac{V_2}{R_2 + \sum_2^n r_n} + \dots + \dfrac{V_n}{R_n + r_n}}{\dfrac{1}{R_1 + \sum_1^n r_n} + \dfrac{1}{R_n + \sum_2^n r_n} + \dots + \dfrac{1}{R_n + r_n} + \dfrac{1}{\Omega}} = V$$

If, in the above equation (6), the condition of $$\Omega >> R_1 + \sum_1^n r_n, R_2 + \sum_2^n r_n, \ldots, R_n + r_n \quad (7)$$

is fully satisfied and the following values $$\left. \begin{array}{l} R_1 + \sum_1^n r_n = 1/\sigma_1 \\ R_2 + \sum_2^n r_n = 1/\sigma_2 \\ \ldots \\ R_n + r_n = 1/\sigma_n \end{array} \right\} \quad (8)$$

are substituted in the equation (6), then the following equations will result:

$$V = \frac{\sigma_1 V_1 + \sigma_2 V_2 + \ldots + \sigma_n V_n}{\sigma_1 + \sigma_2 + \ldots + \sigma_n} \quad (9)$$

The above equation (9) shows that the voltage V indicated on the meter F denotes a weighted mean value of the thermoelectric motive forces $V_1$ to $V_n$ generated by the thermocouples $G_1$ to $G_n$, and also the weight $(\sigma_1, \ldots, \sigma_n)$ in the equation (9) becomes larger as sums of the resistances $R_1$ to $R_n$ of the electric resistors $B_1$ to $B_n$ and the resistances $$\sum_1^n r_n$$

to $r_n$ occurring in the respective sections of the paired metal wires $A_1$, $A_2$ further decrease.

When in the equation (9), the following equation $$\sigma_1 = \sigma_2 = \ldots = \sigma_n \quad (10)$$

is established, then there will be obtained the equation $$V = \frac{V_1 + V_2 \ldots + V_n}{n} \quad (11)$$

The above equation (11) shows that the voltage V indicated on the meter F is a simple means of the thermal electromotive forces $V_1$ to $V_n$ generated by the thermocouples $G_1$ to $G_n$. If, in the equation (8), the following conditions $$\left. \begin{array}{l} R_1 >> \sum_1^n r_n \\ R_2 >> \sum_2^n r_n \\ \ldots \\ R_n >> r_n \end{array} \right\} \quad (12)$$

are fully satisfied, then there result the following equations:

$$\left. \begin{array}{l} \sigma_1 = 1/R_1 \\ \sigma_2 = 1/R_2 \\ \ldots \\ \sigma_n = 1/R_n \end{array} \right\} \quad (13)$$

Thus it will be seen that the effect of resistances occurring in the paired metal wires $A_1$, $A_2$ on the voltage V indicated on the meter F can be disregarded, offering great advantage in practical application.

The key points of the foregoing description will now be summarized. For better understanding, let it be assumed that the resistances $R_1$ to $R_n$ of the electric resistors $B_1$ to $B_n$ do not must vary with temperature, namely, that said resistors $B_1$ to $B_n$ are not sensitive to heat. Then under the circuit arrangement shown in FIG. 1, the electric meter F indicates the electromotive forces corresponding to the temperatures $T_1$ to $T_n$ at the regions where the electric resistors $B_1$ to $B_n$ are disposed. In other words, a thermal electromotive force corresponding to the mean temperature of a region surrounding the paired metal wires $A_1$, $A_2$ is obtained from between the ends $C_1$, $C_2$ of said metal wires $A_1$, $A_2$. If the electric resistors $B_1$ to $B_n$ are chosen to have suitable resistances $R_1$ to $R_n$ for the selected kinds of said paired metal wires $A_1$, $A_2$, then a thermal electromotive force delivered from between the ends $C_1$, $C_2$ of the paired metal wires $A_1$, $A_2$ can be made to correspond to the weighted mean temperature of a region surrounding said metal wires $A_1$, $A_2$, or the simple means temperature of said region, and further the effect of the resistances of the paired metal wires $A_1$, $A_2$ on an electromotive force V occurring between the ends $C_1$, $C_2$ of the paired metal wires $A_1$, $A_2$ can be minimized to be negligible.

Figure 3:
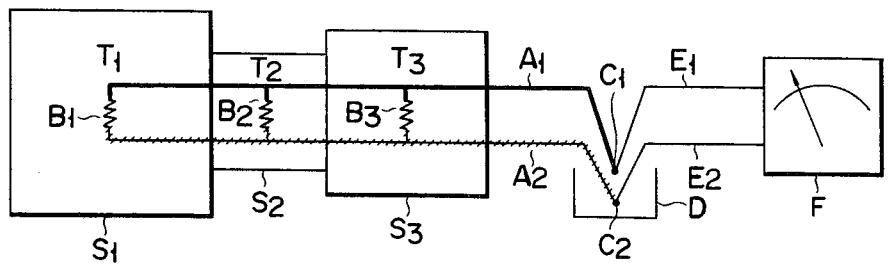
FIG. 3 sets forth the arrangement of the temperature-detecting element of this invention for measuring the temperatures of sites having different areas.

Referring to the circuit of, for example, FIG. 3, in which three electric resistors $B_1$, $B_2$, $B_3$ are connected in parallel between the paired metal wires $A_1$, $A_2$ having given resistances, let it be assumed that the resistances of the electric resistors $B_1$, $B_2$, $B_3$ take the following values:

$$\begin{array}{l} \sigma_1 = 3K \\ \sigma_2 = K \\ \sigma_3 = 2K \end{array} \quad (14)$$

(K is a constant) in the previous equation (9). Then an electromotive force V obtained from between the ends $C_1$, $C_1$ of the metal wires $A_1$, $A_2$, namely, an electromotive force voltage indicated on the metal F may be expressed as follows:

$$V = \frac{3KV_1 + KV_2 + 2KV_3}{3K + K + 2K} = \frac{3V_1 + V_2 + 2V_3}{6} \quad (15)$$

Thus the temperatures $T_1$, $T_2$, $T_3$ of the regions in which the electric resistors $B_1$, $B_2$, $B_3$ are disposed can be detected with weights bearing the ratio of 3:1:2. This means the said temperatures $T_1$, $T_2$, $T_3$ represent the means that said temperatures $T_1$, $T_2$, $T_3$ represent the mean temperatures of three regions $S_1$, $S_2$, $S_3$ having different areas of, for example, 3 $m^2$, 1$m^2$, 2$m^2$. The meter F indicates an electromotive force voltage corresponding to the mean of the temperatures $T_1$, $T_2$, $T_3$ of said three regions $S_1$, $S_2$, $S_3$. If the meter F is of the type capable of indicating a thermoelectric motive force in the form converted to temperature, then the mean of the temperatures of said three regions $S_1$, $S_2$, $S_3$ can be immediately presented.

Where the temperatures $T_1$, $T_2$, $T_3$ of the regions in which the electric resistors $B_1$, $B_2$, $B_3$ are positioned are to be detected with weights bearing the ratio of 3:1:2, then it is advised to let said resistors $B_1$, $B_2$, $B_3$ have such resistances as satisfy the previous equations (14). This procedure provides a mean temperature thus weighted.

Particularly if the paired metal wires $A_1$, $A_2$ have negligibly small resistances compared to the electric resistors $B_1$, $B_2$, $B_3$ and the meter F has an extremely large internal impedance as in, for example, an automatically self-balancing type, then the conditions of the equations (7) and (12) can be satisfied. What is required, therefore, is to let the electric resistors $B_1$, $B_2$, $B_3$ have resistances having the ratio of 1:3:1.5, for example, 100Ω, 300Ω and 150Ω.

Where the electric resistors $B_1$ to $B_n$ used in the circuit of FIG. 1 are insensitive to heat, then it is possible as mentioned above, immediately to find the weighted or simple mean of the temperatures $T_1$ to $T_n$ of the region in which the electric resistors $B_1$ to $B_n$ are set.

There will now be described the temperature-detecting element of this invention from the practical point of view. For the present invention, the equations (3) and (7) should always be satisfied. If, however, the equation (7) is fully met, then the equation (3) is necessarily satisfied. What is required for the invention, therefore, is to provide such conditions as always satisfy the equation (7). The equation (7) means that a sum of the resistances of the paired metal wires $A_1$, $A_2$ forming a thermocouple and the resistance of any of the electric resistors $B_1$ $B_n$ disposed between said metal wires $A_1$, $A_2$ must be negligibly small compared to the internal impedance of the electric meter F. If the ratio which said sum of resistances bears to the impedance of the meter F is about 1:30 or smaller, then the precision of measuring temperature can practically be attained, through the value of said ratio may vary with the actually required precision of measurement. If the equation (12) is satisfied, then it is unnecessary to take into account the resistances of the paired thermocouple metal wires $A_1$, $A_2$ used, offering practical advantage. If a sum of the resistances of the paired thermocouple metal wires $A_1$, $A_2$ is negligibly small compared to the resistance of any of the electric resistors $B_1$ to $B_n$ disposed therebetween, then the equation (12) is naturally satisfied. The ratio which said sum of resistances which bears to the resistance of said electric resistor should practically be preferred to be about 1:30 or smaller in order to obtain satisfactory results in temperature measurement.

Where measurement is made of the mean temperature of a region, electric resistors disposed between two thermocouple metal wires should be insensitive to heat. This heat-insensitive electric resistor may consist of what is commonly so called. A temperature coefficient having an absolute value of preferably 300 ppm/° C or less or more preferably 100 ppm/° C or less provides good results in practical temperature measurement.

Two thermocouple metal wires $A_1$, $A_2$ are not subject to any particular limitation in respect of material. Any material will well serve the purpose, provided it is adapted for use as a component of a thermocouple. Combination of thermocouple component wires is well known to those skilled in the art. The typical examples of said combinations are given below.
chromel-alumel
copper-constantan
chromel-constantan
iron-constantan
platinum-alloy of 90% platinum and 10% rhodium
platinum-alloy of 87% platinum and 13% rhodium
iridium-tungsten
platinel thermocouple Most preferred among those listed above are copper-constantan and chromel-alumel.

If selection of the combination of two thermocouple metal wires is decided, then choice of the kind of heat-insensitive electric resistors being disposed between said metal wires will be obvious to those skilled in the art. Heat-insensitive electric resistors havin a preferably small temperature coefficient ($\alpha$) include, for example, manganin ($\alpha$: about +50 ppm/° C), constantan ($\alpha$: about +50 ppm/° C), cermet ($\alpha$: about ±100 ppm/° C), metal film resistor ($\alpha$: about ±50 to 100 ppm/° C), metal oxide film resistor ($\alpha$: about 100 ppm/° C), nichrome ($\alpha$: about +200 ppm/° C), chromel ($\alpha$: about +400 ppm/° C), and carbon film resistor ($\alpha$: about ±300 ppm/° C). An electric resistor having a larger temperature coefficient than described above may also be available for practical application.

Once selection of the kind of two thermocouple metal wires and that of electric resistors disposed therebetween are decided, then it will be easy to choose an electric meter F having an internal impedance Ω satisfying the equation (7). Said meter F may be an ordinary volt meter such as the aforesaid automatically self-balancing type voltmeter (Ω: about 1 MΩ), electronic tube type voltmeter (Ω: over 100 KΩ), digital voltmeter (Ω: over 1 MΩ).

What calls for attention at this time is that though required, as previously mentioned, for the temperature-detecting element of this invention, consisting of two thermocouple metal wires and a plurality of electric resistors disposed therebetween, the condition of the equation (7) should be considered simply as a guide in selecting the type of electric meter F which is used with said temperature-detecting element.

Figure 4:
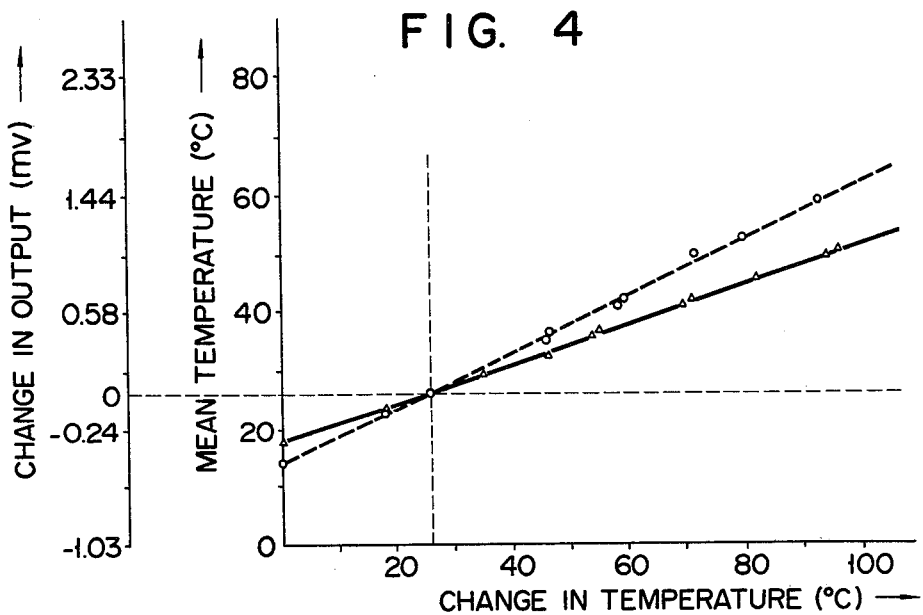
FIG. 4 indicates the mean temperatures actually measured by the temperature-detection element of this invention together with curves representing the theoretical values of means temperatures.

FIG. 4 sets forth the results of experimentally measuring the mean of temperatures at the regions in which three heat-insensitive electric resistors were disposed between copper and constantan thermocouple wires, with the ambient temperature of only one of said electric resistors progressively varied. The triangular marks given in FIG. 4 denote the respective simple mean temperatures and the corresponding thermoelectric motive forces obtained from between the forward ends of said copper and constantan thermocouple wires where all the three electric resistors had a resistance of about 100Ω alike and the ambient temperatures of the two thereof were set at 26° ± 1° C. It is seen from FIG. 4 that the experimental results indicated by the triangular marks fall on a solid line representing the theoretical values of said simple mean temperatures. The white circle marks shown in FIG. 4 indicate the respective weighted mean temperatures and the corresponding thermoelectric motive forces obtained, where the electric resistor disposed at the site whose ambient temperature was progressively varied had a resistance of about 50Ω units and the other factors kept unchanged from those included in the above-mentioned condition. The experimental results indicated by the white circle marks also fall on the broken line of FIG. 4 representing the theoretical values of said weighted mean temperatures. Changes in the thermoelectric motive force are indicated in units of $mV$, with a thermoelectric motive force corresponding to a means temperature of 26° C designated as 0 mV. FIG. 4 shows that substantially no errors take place between the results of experimentally measuring the average temperatures by the temperature-detecting element of this invention and the theoretical values of said mean temperatures. It is further seen that the results of experimentally measuring the weighted mean temperatures present a gradient showing changes 3/2 times larger than those obtained with simple mean temperatures, and that with the condition of measurement taken into account, the mean temperatures were measured with weights bearing the ratio of 2:1:1.

There will now be described the case where it is desired to measure with high sensitivity abnormal local temperature increases or decreases in a region normally having a constant temperature distribution.

Let it be assumed that in FIG. 1, the electric resistors $B_l$ to $B_n$ consist of the negative type thermistors having, for example, an equal resistance and temperature coefficient and that said resistance satisifies the equation (12). If it is assumed that temperatures $T_l$ to $T_n$ in the regions where the electric resistors $B_l$ to $B_n$ are disposed have the same level t, then the resistances $R_l$ to $R_n$ of all the electric resistors $B_l$ to $B_n$ will have an equal value of R to establish the equation (11). The thermoelectric motive forces $V_l$ to $V_n$ generated by the thermocouples $G_l$ to $G_n$ will give forth an equal electromotive force $v$. At this time, an electromotive force V produced across the paired metal wires $A_1$, $A_2$ becomes equal to v as seen from the equation (11).

In other words, if $T_1 = T_2 = \ldots = T_n = t$ under the condition in which the equations (9) and (12) are established, then the following equation results:

$$R_1 = R_2 \ldots R_n = R$$

to establish the equation (11). Since $V_1 = V_2 \ldots V_n = v$, the following equation is derived from the equation (11)

$$V = v \tag{16}$$

Now let it be assumed that the temperature $T_1$ of only the region in which the thermistor $B_1$ is disposed has risen to $t_{up}$. Then the following changes take place in the resistance $R_1$ of the thermistor $B_1$ and the electromotive force $V_1$ generated by the thermocouple $G_1$:

$$T_1 = t \to t_{up}(t_{up} > t)$$

$$V_1 = v \to pv\, (p > 1),$$

p denoting the output characteristic of a thermocouple $$R_1 = R \to R/q\, (q > 1),$$

q denoting the temperature characteristic of a thermistor

For reference, $$T_2 = T_3 \ldots = T_n = t \tag{17}$$

Therefore, an electromotive force $V_t$ produced across the paired thermocouple wires $A_1$, $A_2$ may be expressed as follows from the equations (9), (12) and (13).

$$V_t = \frac{pq\frac{V}{R} + (\frac{n-1}{R})v}{\frac{q}{R} + \frac{(n-1)}{R}} = \frac{pq + (n-1)}{q + (n-1)} \cdot v \tag{18}$$

If, in this case, the electric resistor $B_1$ consists of an ordinary heat-insensitive type whose resistance has little dependence on temperature, then an electromotive force $V_c$ generated between the paired thermocouple metal wires $A_1$, $A_2$ may be expressed as follows from the equation (11):

$$V_c = \frac{p + (n-1)}{n} \cdot v \tag{19}$$

The equations (18) and (19) lead to the following equation:

$$V_t - V_c = \frac{(n-1)(p-1)(q-1)}{n(q+n-1)} \cdot v > 0 \tag{20}$$

$$(\because n \geq 2, p > 1, q > 1)$$

Thus it will be seen that if, in the circuit arrangement of FIG. 1, an electric resistor disposed in the region whose temperature has increased is a heat-sensitive type having negative characteristics, then an electromotive force produced between the paired thermocouple metal wires $A_1$, $A_2$ presents a change larger by the right side term of the above equation (20) than when an electric resistor disposed in the abovementioned region is an ordinary heat-insensitive type having little dependence on temperature, enabling said increased temperature to be indicated in the form of the corresponding increase in the electromotive force.

Further, the following equation is derived from the foregoing equations (16) and (18):

$$V_t - v = (\frac{pq+n-1}{q+n-1} - 1) \cdot v = \frac{(p-1)q \cdot v}{q+n-1} > 0 \tag{21}$$

Namely, it will be seen that an electromotive force generated across the paired thermocouple metal wires $A_1$, $A_2$ presents a change corresponding to the right side term of the above equation (21).

Figure 5:
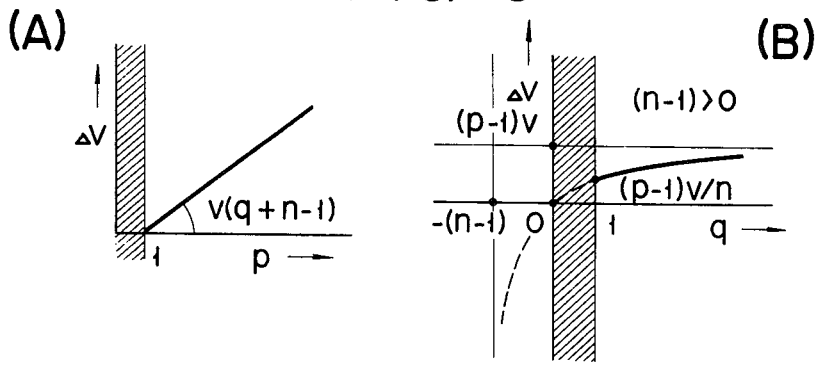
FIGS. 5(A) and 5(B) present the results of qualitatively determining a difference between the electromotive force of the element of this invention for detecting abnormal local temperatures and the electromotive force of the element of the invention for detecting a mean temperature, using different parameters.

Said change $\Delta V (= V_t - v)$ indicates a linear pattern with respect to the parameter p as shown in FIG. 5(A), and presents an increase corresponding to the parameter q as illustrated in FIG. 5(B), though not showing a linear pattern. Namely, the above-mentioned change $\Delta V$ becomes larger as an increase occurs in the thermoelectric power $\epsilon$ (mV/°C) of a thermocouple corresponding to the parameters p and the characteristic temperature B (°K) of a thermistor corresponding to the parameter q.

Where, in FIG. 1, the electric resistors $B_l$ to $B_n$ consist of heat-sensitive resistors having negative characteristics such as negative coefficient thermistors and temperature abnormally rises at one or more local sites within a region having a certain constant temperature distribution, then the resistor or resistors disposed at said one or more sites decrease in resistance. In such case, temperatures at said local sites are detected naturally with weights, which become larger as said temperatures increase. In the above-mentioned case, abnormal local temperature rises lead to sharp increases in the electromotive force produced across the two thermocouple metal wires $A_1$, $A_2$, and consequently can be detected with high sensitivity.

Also if the electric resistors consist of, for example, heat-sensitive resistors having positive characteristics such as positive coefficient thermistors, then abnormal local temperature drops can obviously be detected very quickly likewise.

As apparent from the foregoing description, electric resistors included in a temperature-detecting element which are used in detecting abnormal local temperature changes in a given region need not all be of heat sensitive type. Namely, if at least one of said electric resistors is heat-sensitive and all the others are heat-insensitive, the theoretical principle of this invention can indeed be carried out. However, it is absolutely impossible to find in advance those sites of a given region in which abnormal local temperature changes will take place. It is therefore preferred that electric resistors used in practical application all be of heat sensitive type.

By said heat-sensitive electric resistor is meant a type whose resistance has a large negative or positive temperature dependence. It is practically convenient to define the property of said heat-sensitive electric resistor in terms of its characteristic temperature B (°K). For practical purpose, the heat-sensitive electric resistor is chosen to have a characteristic temperature B ranging between about 1000° and about 5000° K. Therefore, a commercially available heat-sensitive resistor whose characteristic temperature B ranges from about 3000° K to about 3500° K can be used with the temperature-detecting element of this invention. Selection of such heat-sensitive electric resistors will be easy for those skilled in the art. Heat-sensitive electric resistors having negative characteristics include, for example, various types of negative coefficient thermistors whose characteristic temperature B ranges between about 2000 and about 4000, critical temperature resistors (critesistor) and ceramic resistors. Heat-sensitive electric resistors having positive characteristics include, for example, various types of positive coefficient thermistors, silicon electric-resistance thermometers and germanium electric-resistance thermometers.

Figure 6:
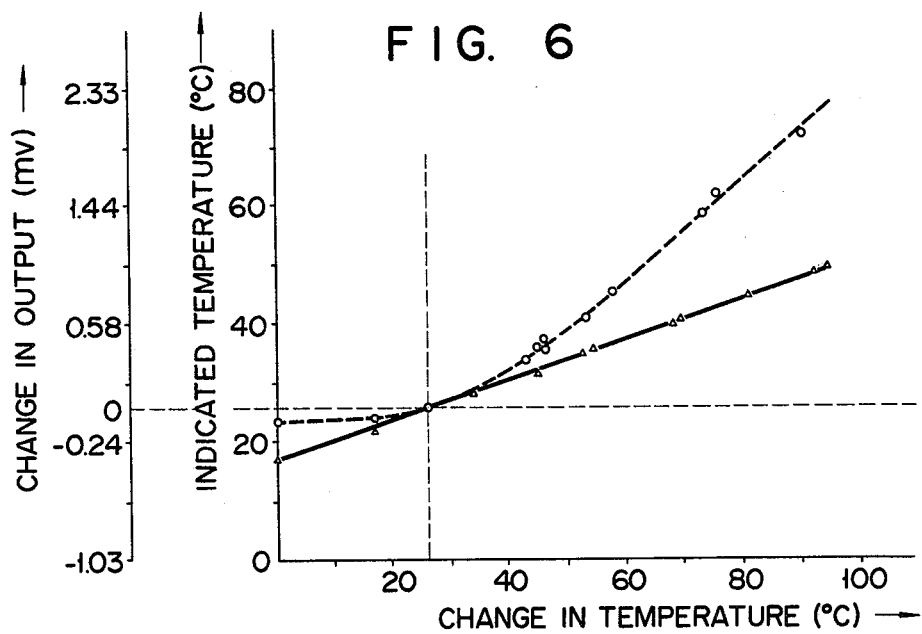
FIGS. 6 and 7 respectively show abnormal local temperature increases and decreases actually determined by the temperature-detecting element of this invention together with curves showing the theoretical values thereof.

FIG. 6 presents the results (indicated by white circle marks) of experimentally measuring abnormal local temperature increases using the temperature-detecting element of this invention in which three thermistors having negative characteristics are disposed between paired copper and constantan metal wires constituting a thermocouple, with the ambient temperature of only one of said thermistors progressively varied. All the thermistors were chosen to have a resistance of about 7 K$\Omega$ at 0° C and a characteristic temperature of about 3400° K. The ambient temperature of two of said three transistors was set at 26° ± 1° C. The broken line of FIG. 6 represents the theoretical values corresponding to the temperatures actually measured.

Figure 7:
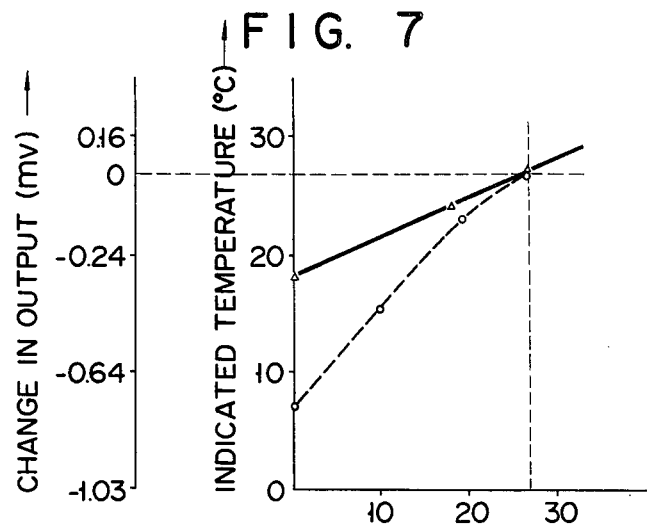

FIG. 7 sets forth the results (indicated by white circle marks) of experimentally measuring abnormal local temperature decreases in the same manner as in FIG. 6, excepting that the three heat-sensitive electric resistors used consisted of thermistors having positive characteristics. The broken line of FIG. 7 denotes the theoretical values corresponding to the temperatures actually measured. Both FIGS. 6 and 7 also show for reference the actually measured temperatures (indicated by triangular marks) and the corresponding theoretical values (represented by a solid line) already presented in FIG. 4.

It is seen from FIGS. 6 and 7 that substantially no difference was observed between the temperatures actually measured by the temperature-detecting element of this invention and the corresponding theoretical values, and also that a temperature-detecting element using heat-sensitive electric resistors has its output more prominently varied with temperature than the type provided with heat-insensitive electric resistors only, thus enabling abnormal local temperature changes to be detected with high sensitivity.

In the temperature-detecting element of this invention for examining abnormal local temperature changes, as in a similar element for determining mean temperatures, the properties, namely, characteristic temperatures or resistances at the same level of temperature of the heat-sensitive electric resistors used may be suitably chosen in accordance with the frequency of abnormal temperature changes expected to occur a number of times in future at the sites of measurement or dangers anticipated from any abnormal local temperature change, should it happen.

Figure 8:
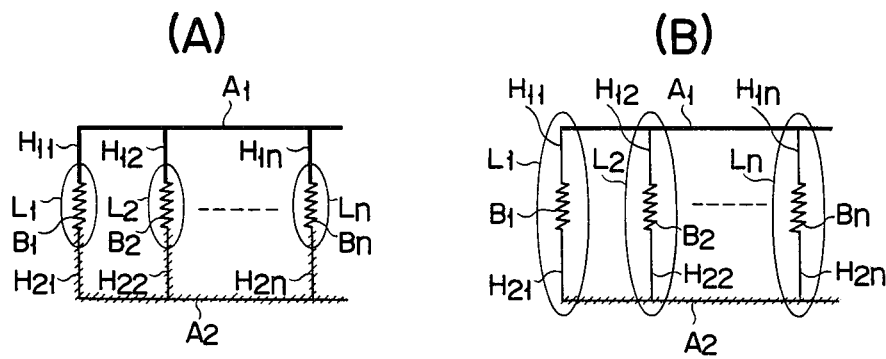
FIGS. 8(A) and 8(B) indicate the different relationships between the kinds of lead wires connecting two metal wires forming a thermocouple and electric resistors used in the temperature-detecting element of this invention, and the kinds of said two metal wires.
Figure 9:
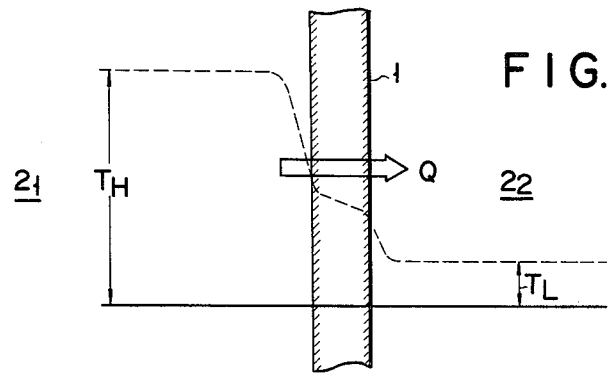
FIG. 9 illustrates the principle by which determination is made of a coefficient of through heat transfer, for example, of structural material.

One group of lead lines $H_{11}$ to $H_{1n}$ and another group of lead lines $H_{21}$ to $H_{2n}$ used with heat-sensitive or heat-insensitive electric resistors $B_l$ to $B_n$ may be formed of material the same as (FIG. 8(A)) that of the corresponding thermocouple metal wires $A_1$, $A_2$ or different therefrom (FIG. 8(B)). If isothermal sections $L_l$ to $L_n$ are reliably present, as shown in FIG. 8(B), in the respective regions, each of which includes an electric resistor, two lead lines and two junctions defined by said electric resistor with the two thermocouple metal wires, then temperature detection can be attained with the same degree of precision even if the lead lines $H_{11}$ to $H_{1n}$, $H_{21}$ to $H_{2n}$ are of different material from the thermocouple metal wires $A_1$, $A_2$ as when said lead lines and metal wires are of the same material. Since, however, an isothermal section is normally small (FIG. 8(A)) in the region in which distribution of temperature occurs at all, application of lead lines $H_{11}$ to $H_{1n}$, $H_{21}$ to $H_{2n}$ formed of the same material as the thermocouple metal wires $A_1$, $A_2$ is preferred, because the results of temperature measurement can be rendered more dependable.

The foregoing description of the principle of this invention refers to the case where a plurality of separate electric resistors were arranged between two metal wires jointly constituting a thermocouple. Namely, said description was made about the so-called lumped constant circuit. However, this invention is also applicable to the so-called distributed constant circuit which is assumed to consist of an infinite number of electric resistors and an infinite number of thermocouples defined between the two metal wires. Throughout this specification and the appended claims, an electric resistor, for example, of linear type, constituting the lumped constant circuit is referred to as a "lumped resistor". An electric resistor, for example, planar or three-dimensional type forming the distributed constant circuit is referred to as a "distributed resistor". Therefore, the term "electric resistor unit" used in the present specification and the appended claims is a comprehensive concept denoting an entirety consisting of two or more parallel connected lumped resistors, at least one distributed resistor, and a combination of at least one lumped resistor and at least one distributed resistor.

The temperature-detecting element of this invention can immediately detect a mean temperature with high sensitivity if the above-defined electric resistor unit disposed between two thermocouple metal wires is of heat-insensitive type and also quickly detect abnormal local temperature changes likewise with high sensitivity if said electric resistor unit contains at least one heat-sensitive electric resistor. The temperature-detecting element of this invention requiring no external constant voltage power source is naturally free from self-explosion.

Figure 10:
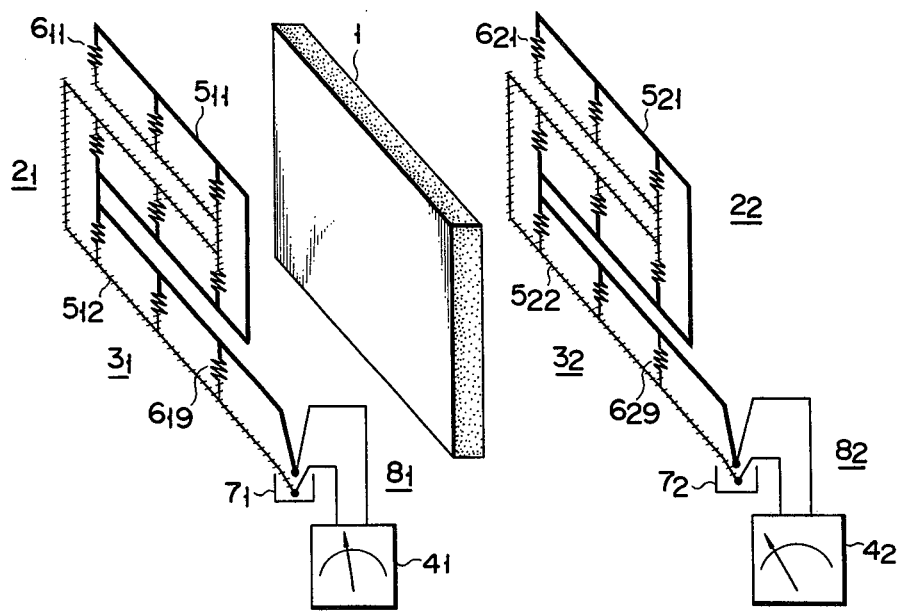
FIG. 10 presents two sets of temperature-detecting apparatus each containing the temperature-detecting element of this invention, as used in practical application.

The embodiments of this invention will now be described by reference to FIGS. 9 to 20. The embodiment of FIG. 10 is an example of applying the temperature-detection element of this invention to measurement of the mean temperature of the open air in determining the coefficient of through heat transfer for the object of evaluating the heat property of structural material, for example, heat-insulating or lagging material.

The process of determining a coefficient of through heat transfer will be briefly described by reference to FIG. 10. Now let it be assumed that the regions $2_1$, $2_2$ lying on both sides of an object material of temperature measurement have temperatures $T_H$ °C, $T_L$ °C ($T_H > T_L$) respectively. Then a temperature gradient occurs as indicated in a broken line in FIG. 9. Namely, a heat flow passes from the higher temperature region $2_1$ through an object 1 of temperature measurement to the lower temperature region $2_2$. The amount of said heat flow is proportional to a difference ($T_H - T_L$) in the temperatures of both regions $2_1$, $2_2$, and varies with the heat property of the object material 1. The ratio which the amount of a heat flow occurring at this time bears to a difference between the temperatures of both regions $2_1$, $2_2$ is referred to as a coefficient U (Kcal/$m^2h$°C) of through heat transfer with Q (Kcal/$m^2h$) takes to denote the amount of a one dimensional heat flow passing through the object material 1 of temperature measurement, then the coefficient U of through heat transfer may be expressed by the following equation:

$$U = \frac{Q}{T_H - T_L} \quad (22)$$

Namely, the coefficient U of through heat transfer is obtained by measuring the temperatures of the regions lying on both sides of the object material 1 and the amount of the one dimensional heat flow.

Usually, the temperature of the region lying on each side of the object material 1 is not uniform therethrough. Therefore, determination of the coefficient U of through heat transfer simply from temperature at a single point in each of the regions $2_1$, $2_2$ lying on both sides of the object material 1 does not give a reliable value. Therefore, general practice is to measure temperatures at a plurality of points in each of said surrounding regions $2_1$, $2_2$ and define the terms $T_H$, $T_L$ of the above equation (22) from the mean value of said measured temperatures. To date, measurement of such mean temperature has been accompanied with considerable difficulties as previously mentioned.

There will now be described by reference to FIG. 10 the embodiment where the temperature-detecting element of this invention is applied in measuring said mean temperature. As illustrated in said FIG. 10, two temperature-detecting elements $3_1$, $3_2$ of this invention used in measuring the mean temperatures in the regions $2_1$, $2_2$ lying on both sides of the object material comprise two pairs of thermocouple metal wires $5_{11} - 5_{12}$, $5_{21} - 5_{22}$ and one group of nine insensitive lumped electric resistors $6_{11}$ to $6_{19}$ disposed at an equal interval between one pair of thermocouple metal wires $5_{11} - 5_{12}$ and another group of nine heat-insensitive lumped electric resistors $6_{21}$ to $6_{29}$ arranged at an equal interval between another pair of thermocouple metal wires $5_{21} - 5_{22}$. The two pairs of thermocouple metal wires $5_{11} - 5_{12}$, $5_{21} - 5_{22}$ are kept at a known temperature, for example 0° C at one end by the corresponding cold junction compensators $7_1$, $7_2$, and connected to the electric meters $4_1$, $4_2$ through lead wires $8_1$, $8_2$. These meters $4_1$, $4_2$ are preferred to be those which indicate outputs from the temperature-detecting elements $3_1$, $3_2$ in the form converted to temperature. One pair of thermocouple metal wires $5_{11} - 5_{12}$ and nine heat insensitive electric resistors $6_{11}$ to $6_{19}$ disposed therebetween jointly constituting one temperature-detecting element $3_1$ are all spatially positioned in the same plane parallel with one side of the object material of temperature measurement. Another pair of thermocouple metal wires $5_{21} - 5_{22}$ and another group of nine heat-insensitive electric resistors $6_{21}$ to $6_{29}$ disposed therebetween jointly constituting another temperature-detecting element $3_2$ are all spatially positioned in the same plane parallel with the opposite side of said object material.

If two pairs of thermocouple metal wires $5_{11} - 5_{12}$, $5_{21} - 5_{22}$ included in said two temperature-detecting elements of the above-mentioned construction consist of a chromel wire 0.65 mm in diameter and about 2 meters long with respect to one of each pair and an alumel wire of the same measurements with respect to the other of each pair, then a sum of resistances of one pair of thermocouple metal wires $5_{11} - 5_{12}$ and that of another pair of thermocouple metal wires $5_{21} - 5_{22}$ are about 6Ω units alike. If, under this condition, each of the resistors $6_{11}$ to $6_{19}$ disposed between one pair of thermocouple metal wires $5_{11}$, $5_{12}$ and each of the resistors $6_{21}$ to $6_{29}$ arranged between another pair of thermocouple metal wires $5_{21}$, $5_{22}$ have an equal resistance within the range of 500 to 5000Ω units, then it is unnecessary to take into count the overall resistance of one pair of thermocouple metal wires $5_1$, $5_2$ and that of another pair of thermocouple metal wires $5_{21}$, $5_{22}$ (namely, the equation (12) is established). Therefore, an electric meter $4_1$ or $4_2$ may be an ordinary voltmeter such as the previously described automatically self-balancing type voltmeter, electric tube type voltmeter, or digital voltmeter. Since as apparent from the foregoing description, the equation (11) is established under the abovementioned condition, the two temperature-detecting elements $3_1$, $3_2$ generate thermoelectric motive forces corresponding to the simple mean temperatures of the regions lying on both sides of the object material 1, and the meters $4_1$, $4_2$ indicate the thermoelectric motive forces thus produced in the form converted to the corresponding simple mean temperatures.

Where measurement is made of atmospheric temperature in the aforesaid manner the resistors $6_{11}$ to $6_{19}$, $6_{21}$ to $6_{29}$ absorb external radiant heat, often leading to errors in temperature measurement. To avoid such undesirable event, it is advised to receive a coil resistor 11 formed, as shown in FIG. 11(A) by winding an insulated resistor, for example, an enameled constantan wire 9 about a Teflon bobbin 10 or a compact metal oxide film type resistor 12 (FIG. 11(B)) having a temperature coefficient of, for example, less than 100 ppm/° C in a cylindrical case 14 (FIG. 11(D)) provided with end plates 13 and elevated in surface reflectiveness by means of mirror finishing or plating with gold or chromium. Further, each of the above-mentioned end plates 13 whose front view is given in FIG. 11(C), should preferably be bored with a plurality of holes, and the bobbin 10 should advisably be notched in both peripheral portions as illustrated in FIG. 11(C). Moreover, one of the lead lines 15 of the above-mentioned resistor 11 or 12 is chosen to be of the same material as one component of the two pairs of thermocouple metal wires $5_{11} - 5_{12}$, $5_{21}$ $-5_{22}$ and the other of said lead wires 15 is chosen to be of the same material as the other component of said two pairs of thermocouple metal wires $5_{11} - 5_{12}$, $5_{21} - 5_{22}$. This arrangement renders the result of temperature measurement prominently reliable.

Thus the mean temperatures of the regions surrounding the temperature-detecting elements $3_1$, $3_2$, namely, the mean temperature $T_H$, $T_L$ of the regions $2_1$, $2_2$ of the atmosphere can be easily and immediately determined with high precision by said temperature-detecting elements $3_1$, $3_2$. When the amount Q of one dimensional heat flow passing through the object material 1 at that time is measured by the prescribed process, then the coefficient U of through heat transfer of the object material 1 can be determined by the aforesaid equation (22) from the mean atmospheric temperatures $T_H$, $T_L$ and the amount Q of one dimensional heat flow.

Figure 12:
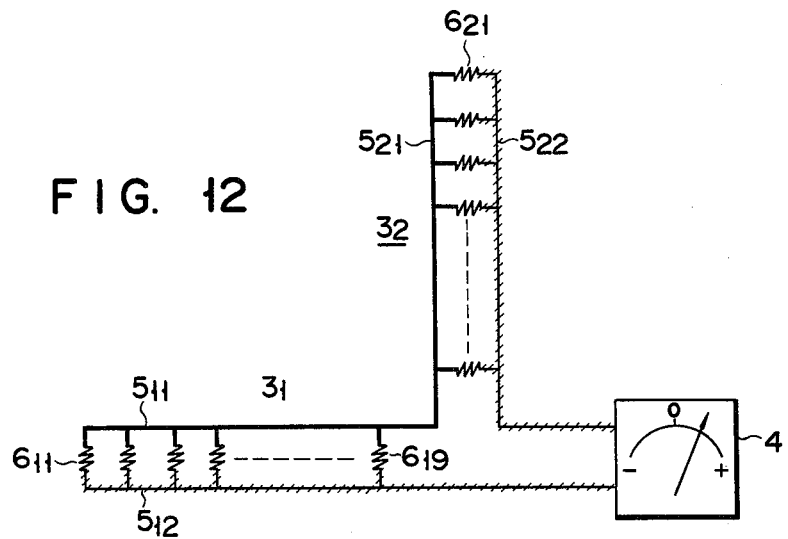
FIG. 12 is a modification of the temperature-detecting element of this invention shown in FIG. 10.
Figure 11:
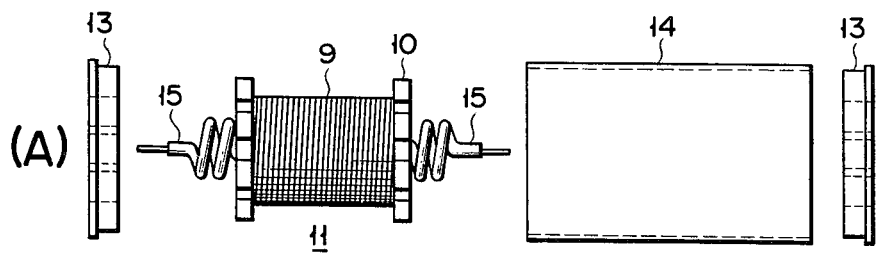
FIGS. 11(A) to 11(D) indicate the structural members of an electric resistor used with the temperature-detecting element of this invention shown in FIG. 10.
Figure 11:
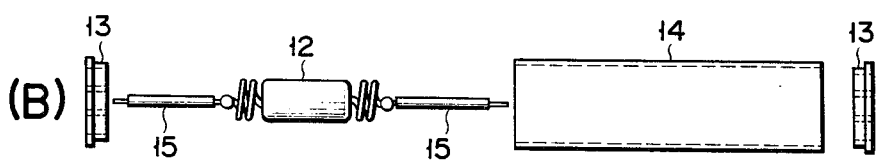
Figure 11:
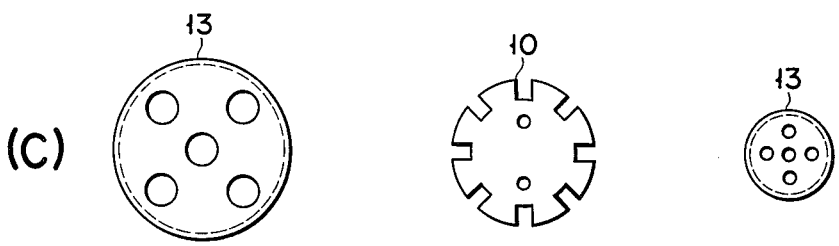
Figure 11:
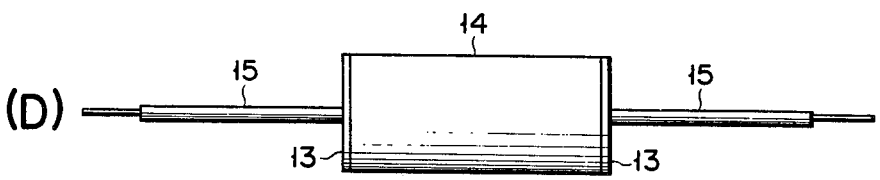

In the foregoing embodiment, the temperature-detecting elements $3_1$, $3_2$ were connected to the corresponding electric meters $4_1$, $4_2$ to determine the mean temperatures $T_H$, $T_L$ of the atmospheric regions $2_1$, $2_2$ lying on both sides of the object material 1, thereby calculating a difference $(T_H - T_L)$ between both mean temperatures. It is however possible differentially to connect both temperature-detecting elements $3_1$, $3_2$ as shown in FIG. 12 and indicate a differential output on a zero center type electric meter 4. This arrangement enables a difference $(T_H - T_L)$ between the mean temperatures of both atmospheric regions $2_1$, $2_2$ to be immediately determined.

In the above-mentioned embodiment, nine electric resistors having an equal resistance were disposed between a pair of thermocouple metal wires to measure a simple mean temperature. However, the number of said resistors need not be limited to that used. For example, the resistors may be provided in any other number, for example, five. If the number (e.g. five) of resistors used can not divide an object region of temperature measurement into equal areas, then it is advised to apply such weights as correspond to the divided areas to the resistances of the resistors disposed in the respective sections, thereby determining a weighted mean average.

In the aforesaid embodiment, the temperature-detecting element was applied in measuring a mean atmospheric temperature to define the coefficient of through heat transfer of an object material. However, the application of the subject temperature detecting element is not limited to such use. But said element can be widely adapted in determining the mean temperature of for example, a furnace during a batch process or water filled in a bathtub.

Figure 13:
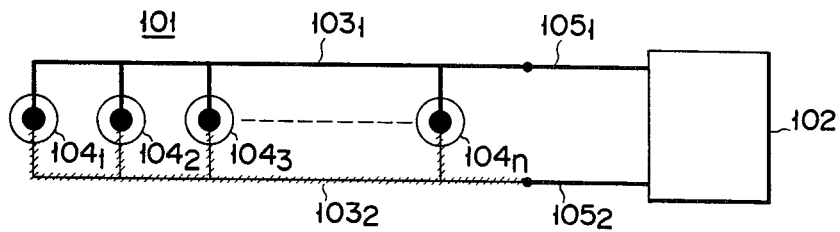
FIG. 13 is another embodiment using the temperature detecting element of this invention.

FIG. 13 shows an embodiment where an abnormal local temperature change-detecting element according to this invention is applied to an alarm device for detecting the occurrence of, for example, a fire or leakage of a bath from an electric furnace and giving an alarm.

The output terminal of a temperature-determining element 101 generating a thermoelectric motive force is connected to an alarm circuit 102 which gives an alarm when said thermoelectric motive force rises above the preset level.

The temperature-detecting element 101 consists of a pair of thermocouple metal wires, for example, a copper wire $103_1$ and a constantan wire $103_2$ and an n number of heat-sensitive resistors $104_1$ to $104_n$ parallel connected therebetween at an equal interval. The paired thermocouple metal wires $103_1$, $103_2$ of different materials are connected at one end to the alarm circuit 102 through the corresponding copper lead lines $105_1$, $105_2$.

Figure 14:
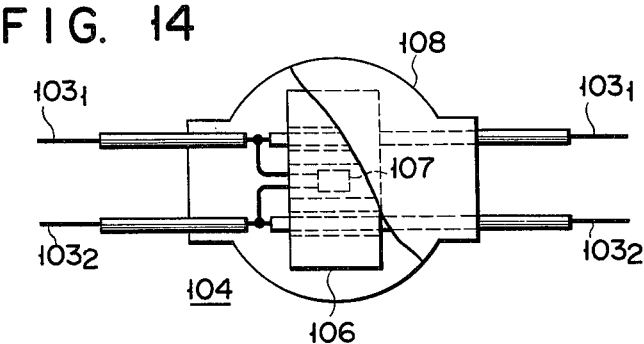
FIGS. 14(A) and 14(B) present the structural members of the electric resistors used with the temperature-detecting element of FIG. 13.
Figure 15:
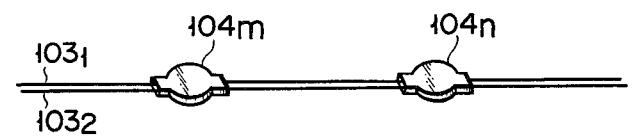
FIG. 15 shows an equivalent circuit of the arrangement of FIG. 13.

As illustrated in FIG. 14, each of the heat-sensitive electric resistors $104_1$ to $104_n$ comprises an aluminium block 106 measuring 20 mm × 10 mm × 2 mm and bored with three lengthwise through holes 1.2 mm in diameter, a thermistor 107 having negative characteristics which is inserted into the central hole and a pair of thermocouple metal wires $103_1$, $103_2$ of different materials inserted into both side holes, with both ends of the thermistor 107 connected to said metal wires $103_1$, $103_2$ of different materials, thereby reliably transmitting the temperature of an object material of temperature measurement to the thermistor 107 and paired thermocouple metal wires $103_1$, $103_2$ of different materials. The outside of the aluminium block 106 is coated with heat-resistant rubber covering 108 such as silicone rubber or fluorine-base rubber so as to attain the mechanical protection and fixation of the thermistor 107 and paired thermocouple metal wires $103_1$, $103_2$ of different materials, equalize the temperature of the object material and that of the aluminium block 106 by the heat retentivity of said covering and improve the adhesivity of the aluminium block 106 to the object material. The heat-sensitive electric resistors $104_1$ to $104_n$ are located at the required sites.

If, under the above-mentioned arrangement, the resistances of the paired thermocouple metal wires $103_1$, $103_2$, the resistances ($R_1$ to $R_n$) of the heat-sensitive electric resistors $104_1$ to $104_n$ at normal temperature and the internal impedance ($R_0$) of the alarm circuit 102 are chosen to have suitable values to satisfy the condition of the equation (7), then the equation (9) is established. If abnormal local temperature rises occur at some of the sites in which the heat sensitive electric resistors $104_1$ to $104_n$ are positioned, then the paired thermocouple metal wires $103_1$, $103_2$ produce sharply increased thermoelectric motive forces corresponding to said temperature rises.

As previously mentioned, copper lead lines $105_1$, $105_2$ are connected to the paired thermocouple metal wires $103_1$, $103_2$ respectively at one end to form a differential thermocouple circuit. If, in this case, the resistances of the heat-sensitive electric resistors $104_1$ to $104_n$ at normal temperature are so chosen as to satisfy the condition of the equation (12), then the resistances of said paired thermocouple metal wires $103_1$, $103_2$ and lead lines $105_1$, $105_2$ can be disregarded. With $V_0$ is taken to denote a thermoelectric motive force occurring at the junction of the constantan line $103_2$ and lead line $105_2$ and $V_1$ to $V_n$ thermoelectric forces generated at the thermocouples formed by the resistors $104_1$ to $104_n$ and corresponding parts of metal wires $103_1$, $103_2$, an equivalent circuit including the alarm circuit 102 and the temperature-detecting element 101 presents a form shown in FIG. 15. With V taken to denote the voltage occurring across the two output terminals of the temperature-detecting element 101, namely, the voltage impressed on the alarm circuit 102, then the following equation results:

$$\frac{V_1}{R_1} + \frac{V_2}{R_2} \cdots + \frac{V_n}{R_n} \qquad (23)$$

$$= (\frac{1}{R_0} + \frac{1}{R_1} + \frac{1}{R_2} \cdots + \frac{1}{R_n})V - (\frac{1}{R_1} + \frac{1}{R_2} \cdots + \frac{1}{R_n})V_0$$

If the equation $$V_1 = V_2 \ldots = V_n = V_0 \quad (24)$$

is established in the above equation (23), then the following equation results:

$$V = 0 \quad (25)$$

Where, therefore, the temperatures of the regions surrounding the temperature detecting element 101 equally rise, then no thermoelectric motive force is generated across the two output terminals of the temperature-detecting element 101. Only where any abnormal local temperature increase takes place in the regions surrounding the temperature-detecting element 101, then a sharply elevated thermoelectric motive force arises according to said local temperature increase. If said thermoelectric motive force exceeds a prescribed level, then the alarm circuit 102 sends forth an alarm. Namely, where the temperature of an entire room or electric furnace rises from a given level to a higher one, the alarm circuit 102 does not give any alarm. Only where any abnormal local temperature increase occurs in the room or electric furnace, it is detected with high sensitivity with the resultant alarm.

The temperature-detecting element 101 of this invention can detect with high sensitivity abnormal local temperature increases occurring in a region surrounding said temperature-detecting element 101 which are caused, for example, by a fire or leakage of molten mass from an electric furnace simply by setting an $n$ number of heat-sensitive electric resistors $104_1$, to $104_n$ spatially at prescribed sites between a pair of thermocouple metal wires $103_1$, $103_2$. Since said metal wires $103_1$, $103_2$ generate a thermoelectric motive force corresponding to any abnormal temperature increase taking place in their surrounding, any external voltage source need not be provided, and moreover the subject temperature-detecting element 101 can be made free from self-explosion. As previously mentioned, only where an abnormal local temperature increase occurs in the surrounding of the subject temperature-detecting element 101, the thermocouple metal wires $103_1$, $103_2$ jointly produce a sharply increased thermoelectric motive force corresponding to said abnormal local temperature increase. Therefore, even if the alarm circuit 102 consists of the type which is not operated upon detection of a gradient of changes in an output thermoelectric motive force from the thermocouple metal wires $103_1$, $103_2$, namely, an amount of said change per unit time, but is of such simple arrangement as is actuated only upon detection of a change exceeding the prescribed level of an output from said metal wires $103_1$, $103_2$, any erroneous alarm can be prevented from being given.

In the foregoing embodiment wherein a differential thermocouple circuit is formed by the paired metal wires $103_1$, $103_2$ and lead lines $105_1$, $105_2$, the temperature-detecting element 101 generates a thermoelectric motive force across its two output terminals only where an abnormal local temperature increase arises in the surrounding of said temperature-detecting element 101. Therefore, a thermocouple electromotive force $V_0$ appearing at a differential junction, namely, a junction between the thermocouple metal wire $103_2$ and lead line $105_2$ is weighted about n times as compared with thermoelectric motive forces $V_1$ to $V_n$ occurring at the junctions between the heat-sensitive electric resistors $104_1$ to $104_n$ and paired thermocouple metal wires $103_1$, $103_2$.

Figure 16:
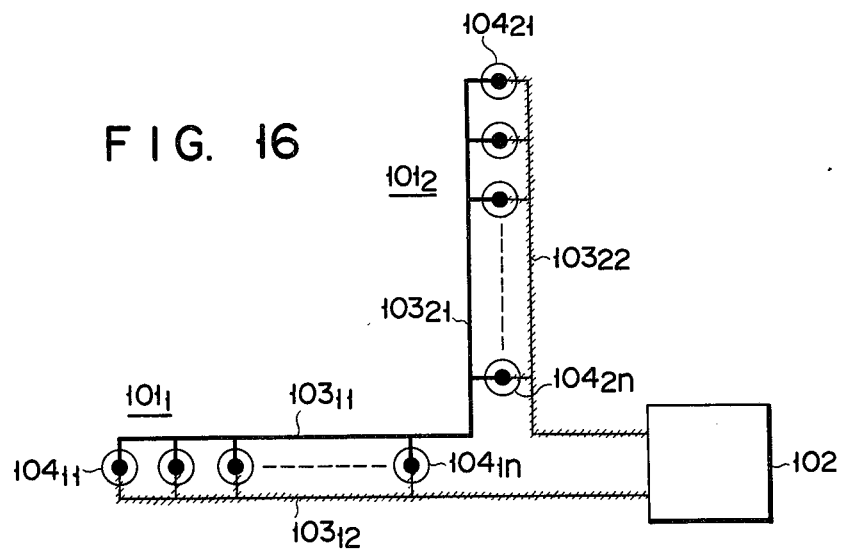
FIGS. 16, 17 and 18 are other modifications of the temperature-detecting element of the invention shown in FIG. 13.

Therefore, measurement of temperature changes at said differential junction should be carried out with due consideration given to the above-mentioned fact. To this end, it is advised to provide a pair of temperature-detecting elements $101_1$, $101_2$ of the same arrangment, as shown in FIG. 16, one of which comprises paired thermocouple metal wires $103_{11}$, $103_{12}$ and an n number of heat-sensitive electric resistors $104_{11}$ to $104_{1n}$ and the other of which comprises paired thermocouple metal wires $103_{21}$, $103_{22}$ and an n number of heat-sensitive electric resistors $104_{21}$ to $104_{2n}$, differentially connect said paired temperature-detecting elements $101_1$, $101_2$, supply a differential output to the alarm circuit 102, and cause said circuit 102 to give different forms of alarm according to the polarity of said differential output. This arrangement prevents a thermoelectric motive force occurring at the differential junction from being weighted $n$ times as compared with the electromotive force generated by the thermocouple, part of which is constituted by the heat-sensitive electric resistors $104_1$ to $104_n$. Further, the alarms given by the alarm circuit 102, the forms of which vary with the polarities of differential outputs from said temperature-detecting elements $101_1$, $101_2$ make it possible to find which of the regions provided with the paired temperature-detecting elements $101_1$, $101_2$ presented an abnormal local temperature increase. Where, however, abnormal local temperature increases of substantially the same degree occur in both regions in which the temperature-detecting elements $101_1$, $101_2$ are disposed, then differential outputs from said elements $101_1$, $101_2$ offset each other, eventually resulting in the absence of any differential output. Therefore, this fact should be taken into account in applying the embodiment of FIG. 16. It is also possible directly to draw out a thermoelectric motive force occurring across the paired thermocouple metal wires $103_1$, $103_2$ instead of providing a differential junction between said metal wires $103_1$, $103_2$ and lead lines or differentially connecting the paired temperature-detecting elements $101_1$, $101_2$. If, in this case, the alarm circuit 102 is of the type which is operated upon detection of a gradient of changes in outputs from said paired temperature-detection elements $101_1$, $101_2$, namely, an amount of temperature change per unit time or of the type which is actuated only upon detection of a change exceeding a prescribed level of an output thermoelectric motive force from said circuits $101_1$, $101_2$, then the former type of alarm circuit 102 enables the paired temperature-detecting elements $101_1$, $101_2$ to detect any sharply increasing overall temperature and the latter type of alarm circuit 102 enables said elements $101_1$, $101_2$ to detect an overall temperature increase above a prescribed level.

Figure 17:
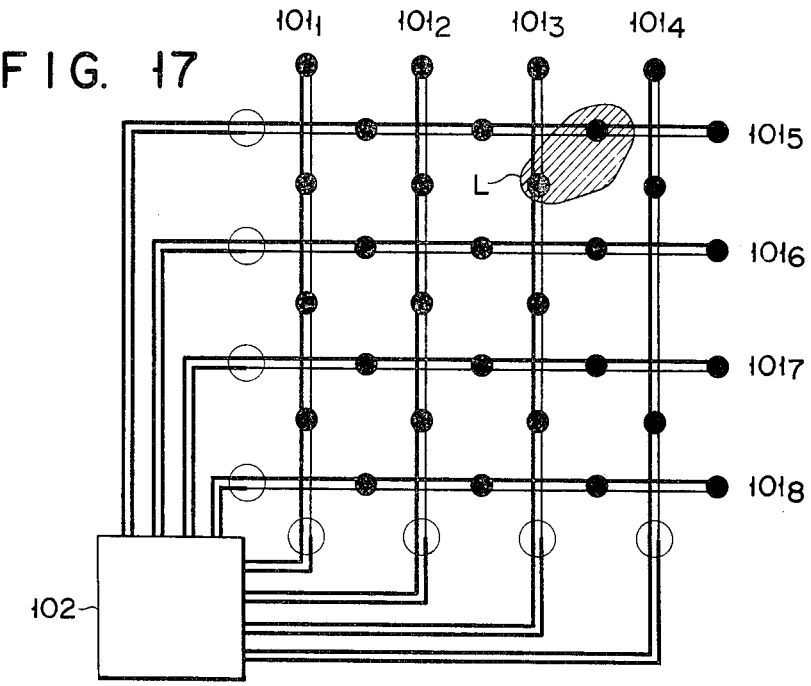
Figure 18:
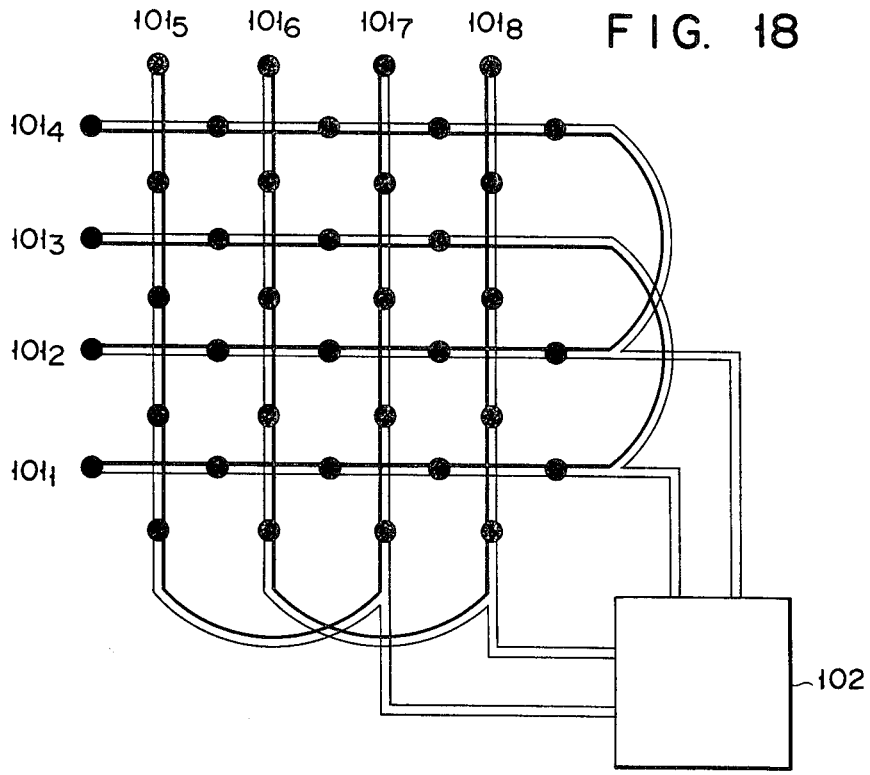

Any of the foregoing embodiments has failed exactly to point out that site within the surrounding of a temperature-detecting element where an abnormal local temperature increase took place, though capable of simply detecting the occurrence of said abnormal local temperature increase. If a plurality of (for example, eight) temperature-detecting elements $101_1$ to $101_8$ of the same arrangement are set, as illustrated in FIG. 17, in the matrix form and each pair of thermocouple metal wires and the corresponding lead lines are differentially connected, or every two of the eight temperature-detecting elements are differentially connected as shown in FIG. 18, and differential outputs are supplied to the alarm circuit 102, then it is possible to detect not only any abnormal local temperature increase in a region surrounding all said temperature-detecting elements $101_1$ to $101_8$ but also the exact site at which said abnormal local temperature increase took place. Referring to FIG. 17, if all differential outputs from the eight temperature-detecting elements $101_1$ to $101_8$ have a positive polarity, then it is possible to see that abnormal local temperature increases took place at the sites marked by black circles in which the heat-sensitive resistors are positioned. And if all differential outputs from said elements $101_1$ to $101_8$ have a negative polarity, then it shows that abnormal local temperature increases occurred at the sites marked by white circles in which the heat-sensitive resistors are disposed. Further, if all the temperature-detecting elements $101_1$ to $101_8$ produce differential outputs of positive polarity, the temperature-detecting elements $101_3$, $101_5$ generate large differential outputs, the temperature-detecting elements $101_4$, $101_6$ give forth small differential outputs, and the other temperature-detecting elements $101_1$, $101_2$, $101_7$, $101_8$ present zero differential outputs, then an abnormal local temperature increase is shown to have taken place at a site L marked by a hatching which extends over the temperature-detecting elements $101_3$, $101_5$ and lies near the temperature-detecting elements $101_4$, $101_6$.

In all the foregoing embodiments, thermistors of negative characters disposed between paired thermocouple metal wires were chosen to have an equal resistance at the same temperature and characteristic temperature B. However, the resistances or characteristic temperatures of said thermistors may be so chosen to have such values as match the expected frequency of abnormal local temperature increases at the sites of temperature measurement or anticipated dangers resulting from any of said abnormal local temperature increases. This procedure enables the above-mentioned resistors or characteristic temperatures B of the thermistors to be weighted in degree corresponding to the expected frequency of abnormal local temperature increases or the anticipated dangers caused by any of said abnormal local temperature increases.

In the foregoing embodiments, the heat-sensitive electric resistors consisted of thermistors of negative characters to detect abnormal local temperature increases. However, said heat-sensitive electric resistors may be formed of thermistors of positive characteristics. This type of thermistor can detect an abnormal local temperature decrease with high sensitivity.

In one of the foregoing embodiments, the temperature-detecting element of this invention was applied to an alarm device for giving forth an alarm upon detection of a fire or leakage of molten mass from an electric furnace. However, application of this invention is not limited to said embodiment. The invention is further applicable to an incubator to detect abnormal local temperature increases or decreases therein with high sensitivity, thereby prominently elevating the safety of the incubator.

The temperature-detecting element of this invention is also applicable, for example, to an electric blanket. This application is effected in the following manner. There is first provided a thermocouple consisting of a pair of metal wires $103_1$, $103_2$ of different materials, one of which is constituted for example, by the heater $103_2$ (FIG. 19) of the electric blanket. Said paired thermocouple metal wires $103_1$, $103_2$ of different materials are embedded at an equal interval in a code 111 made of conductive plastic material having negative temperature characteristics. A cold junction compensator 112 is connected to the thermocouple metal wires $103_1$, $103_2$ respectively at one end to form a temperature-detecting element 101 concurrently acting as a heat element. An output from the temperature-detecting element 101 is supplied to a power control circuit 113, which is connected to the blanket heater $103_2$ to control the operation of a power source 114 and in consequence power supply to the blanket heater $103_2$. This arrangement detects with high sensitivity abnormal local temperature increases caused by the twisting or bending of the electric blanket, thereby immediately cutting off power supply to the blanket heater $103_2$, and consequently preventing the occurrence of various accidents resulting from abnormal local temperature increases, such as the outbreak of flames from the electric blanket or burns sustained by the user with the resultant prominent increase in the safety of the electric blanket. Where an abnormal temperature increase takes place in the whole of the blanket due to, for example, the failure of the temperature control device, then this arrangement of the electric blanket can detect said abnormal overall temperature increase and suppress any resultant accident.

Figure 19:
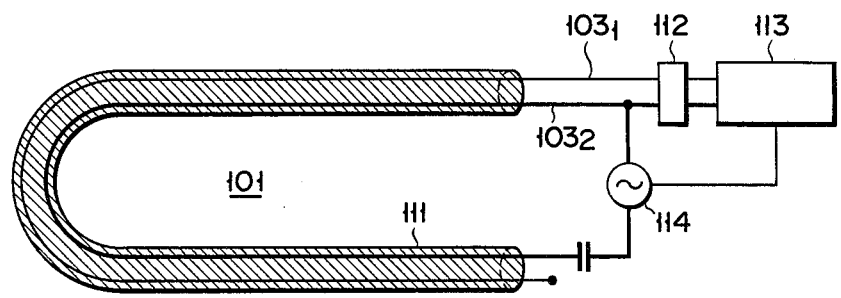
FIG. 19 is another embodiment using the temperature detecting element of the invention.
Figure 20:
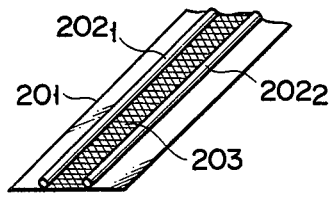
FIGS. 20(A) and 20(B) illustrate different forms of the temperature-detecting element of the invention having distributed resistors.
Figure 20:
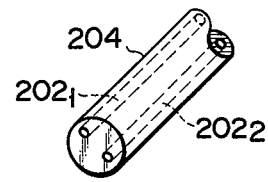

According to all the foregoing embodiments except for that of FIG. 19, the previously defined resistor unit disposed between a pair of thermocouple metal wires consists of separate electric resistors, namely, lumped resistors, but obviously may be formed of a distributed resistor. A temperature-detecting element including said distributed resistor may be constructed by, as shown in FIG. 20(A), mounting a pair of thermocouple metal wires $202_1$, $202_2$ on a piece of insulation sheeting made of paper or polyvinyl chloride, and coating an interspace between said metal wires $202_1$, $202_2$ with heat-insensitive or heat-sensitive electric resistor paint carbon (that is, distributed resistor) customarily used, for example, as a planar heating element, or embedding, as illustrated in FIG. 20(B), paired thermocouple metal wires $202_1$, $202_2$ at an equal interval in a code 204 made of heat-insensitive or heat sensitive conductive plastic material (that is, distributed resistor). Both arrangements described above can detect temperature accurately without errors.

The temperature-detecting element of this invention has a very simple arrangement consisting, as previously mentioned, of a pair of metal wires jointly forming a thermocouple and an electric resistor unit disposed between said metal wires, detects temperature with high sensitivity, and moreover is constructed free from self-explosion due to omission of an external voltage power source, thus offering great safety.

What we claim is:

1. An element for detecting a weighted mean temperature of a given region comprising two metal wires constituting a thermocouple, and electric resistor means consisting of a plurality of heat-insensitive resistors each electrically connected between said two metal wires and each within a different defined section in said region, each resistor having a temperature coefficient of less than 300 ppm/° C absolute, wherein the resistance of said resistor means is at least 30 times the sum of resistance of said two metal wires, and the resistance ratio between any two resistors is the reciprocal of the ratio between the areas of the two sections within which the said two resistors are respectively disposed.

2. The element according to claim 1, wherein said resistors are lumped resistors.

3. The element according to claim 2, wherein said resistors are formed of constantan.

4. The element according to claim 1, wherein said resistors are distributed resistors.

5. An element for detecting an abnormal local temperature change in a given region comprising two metal wires constituting a thermocouple, and an electric resistor means consisting of a plurality of heat-sensitive resistors each electrically connected between said two metal wires and each within a different defined section in said region, wherein the resistance of said resistor means is at least 30 times the sum of resistance of said two metal wires, and the resistance ratio between any two resistors is the reciprocal of the ratio between the areas of the two sections within which the said two resistors are respectively disposed.

6. The element according to claim 5, wherein said resistors are lumped resistors.

7. The element according to claim 6, wherein said resistors are negative characteristic resistors having a characteristic temperature of 1000° to 5000° K.

8. The element according to claim 6, wherein said resistors are positive characteristic resistors.

9. The element according to claim 5, wherein said resistors are distributed resistors.

10. The element according to claim 9, wherein said resistors are negative characteristic resistors having a characteristic temperature of 1000° to 5000° K.

11. The element according to claim 10, wherein said resistors are thermistors.

12. The element according to claim 9, wherein said resistors are positive characteristic resistors.

13. An apparatus for detecting a weighted mean temperature of a given region comprising two metal wires constituting a thermocouple, an electric resistor means consisting of a plurality of heat-insensitive resistors each electrically connected between said two metal wires and each within a different defined section in said region, each resistor having a temperature coefficient of less than 300 ppm/° C absolute, and a meter connected to said two metal wires at one end thereof so as to measure a voltage across the ends of said two metal wires, wherein the internal impedance of said meter is at least 30 times a total of the resistance of said resistors and the sum of resistance of said two metal wires, the resistance of said resistor means is at least 30 times the sum of resistance of said two wires, and the resistance ratio between any two resistors is the reciprocal of the ratio between the areas of the two sections within which the said two resistors are respectively disposed.

14. The apparatus according to claim 13, wherein said resistors are lumped resistors.

15. The apparatus according to claim 13, wherein said resistors are distributed resistors.

16. An apparatus for detecting an abnormal local temperature change in a given region comprising two metal wires constituting a thermocouple, an electric resistor means consisting of a plurality of heat-sensitive resistors each electrically connected between said two metal wires and each within a different defined section in said region, and a meter connected to said two metal wires at one end thereof so as to measure a voltage across the ends of said two metal wires, wherein the internal impedance of said meter is at least 30 times a total of the resistance of said resistors and the sum of resistance of said two metal wires, the resistance of said resistors is at least 30 times the sum of resistance of said two metal wires, and the resistance ratio between any two resistors is the reciprocal of the ratio between the areas of the two sections within which the said two resistors are respectively disposed.

17. The apparatus according to claim 16, wherein said resistors are lumped resistors.

18. The apparatus according to claim 16, wherein said resistors are distributed resistors.

19. The apparatus according to claim 18, wherein said resistors are negative characteristic thermistors, having a characteristic temperature of 1000° to 5000° K.

20. The apparatus according to claim 18, wherein said resistors are positive characteristic resistors.

* * * * *